United States Patent [19]

Köhler et al.

[11] 3,976,762

[45] Aug. 24, 1976

[54] MULTI-ORGAN TECHNETIUM COMPLEXES PRODUCTION AND USE THEREOF

[75] Inventors: Günter A. Köhler, Grant Township, Washington County; Gary M. Pestel, Mahtomedi, both of Minn.

[73] Assignee: Minnesota Mining and Manufacturing Company, St. Paul, Minn.

[22] Filed: July 5, 1974

[21] Appl. No.: 485,839

[52] U.S. Cl. .............................. 424/1; 252/301.1 R; 252/301.15; 260/502.5; 424/211
[51] Int. Cl.² ..................... A61K 43/00; G21H 5/02
[58] Field of Search ............. 424/1, 211; 260/429 R, 260/502.5; 252/301.1 R, 301.15

[56] References Cited
UNITED STATES PATENTS

| | | | |
|---|---|---|---|
| 3,600,470 | 8/1971 | Lewis | 260/429 R X |
| 3,725,295 | 4/1973 | Eckelman et al. | 252/301.1 R |
| 3,735,001 | 5/1973 | McRae et al. | 424/1 |
| 3,851,044 | 11/1974 | Adler et al. | 424/1 X |
| 3,852,414 | 12/1974 | Adler et al. | 424/1 |

OTHER PUBLICATIONS

Subrumanian et al., Radiology, vol. 102, Mar., 1972, pp. 701–704.

*Primary Examiner*—Benjamin R. Padgett
*Assistant Examiner*—Christine M. Nucker
*Attorney, Agent, or Firm*—Alexander, Sell, Steldt & DeLaHunt

[57] ABSTRACT

Chemical complexes, useful as radiopharmaceuticals, are formed by reacting technetium-99m with substituted or unsubstituted alkyl monophosphonic acids and certain ester derivatives thereof. The complexes are formed by reducing pertechnetate ion chemically or electrolytically in the presence of the phosphonic acid. By chemical modification of the phosphonic acid complexing agent, it is possible to "tailor" complexes for kidney, liver or bone imaging. The complexes are normally used in a physiologically acceptable aqueous medium.

20 Claims, No Drawings

MULTI-ORGAN TECHNETIUM COMPLEXES PRODUCTION AND USE THEREOF

FIELD OF THE INVENTION

This invention relates to chemical complexes of the radioactive, metastable isotope technetium-99m (Tc-99m) wherein the complexing agents are monophosphonic acids and certain ester derivatives thereof. An aspect of this invention relates to a process for preparing the complexes and a preferred biologically sterile, substantially isotonic medium containing the complexes. A further aspect of this invention relates to the use of the products of the invention as kidney, liver or bone imaging agents.

BACKGROUND OF THE INVENTION

The art of radiochemistry has found many applications in the fields of boiological research and medical diagnosis. It is well known that certain radioactive preparations, when introduced into a biological system, will localize in specific organs, tissues or skeletal material. With radiation detecting devices, it is then possible to visualize these target areas, and thereby monitor the functioning of certain organs, for example, the kidney and liver, or to diagnose aberrations or pathological conditions existing in certain tissues, for example, the skeleton.

The metastable isotope Tc-99m is particularly desirable for use in radiopharmaceutical preparations because of its unique combination of nuclear properties. This nuclide has a high specific activity (99 percent gamma radiation at 140 keV), which makes possible the visualization of deep organs, yet the radiation is easily collimated. Tc-99m also has a conveniently rapid rate of decay (6 hour half-life) which is ideal for most diagnostic purposes. The absence of beta emissions from Tc-99m reduces the radiation hazard to the patient, and although Tc-99m's decay product Tc-99 is a beta emitter, it has a very long half-life, and, thus, radiation from residual amounts of this material is of little consequence to the patient. In recent years, Tc-99m has become readily available to laboratories through the use of a molybdenum-99 (Mo-99) generator from which Tc-99m is obtained as a radioactive decay product.

Although Tc-99m would appear to be an ideal material for use in radiopharmaceuticals, a problem arises in finding suitable carriers of ligands which will form stable complexes with the nuclide and impart to it the desired organ specificity. Complexes of Tc-99m must also exhibit minimal toxic side effects and be safely eliminated from the body.

A number of complexes of Tc-99m have been introduced in recent years which have predictable stability and organ specificity. Known complexes of Tc-99m are primarily designed for the study of one organ system. For example, Tc-99m complexed with pencillamine and acetazolamide, described in U.S. Pat. No. 3,743,913, is primarily useful as a kidney scanning agent. Tc-99m-sulfur colloid complex, described in British Pat. No. 1,305,035, is designed for liver scanning; and Tc-99m-labeled polyphosphate, described in Radiology 102: 701–704, Mar. 1972, is generally employed as a bone imaging agent.

Several currently available Tc-99m complexes for bone imaging utilize phosphorus-containing ligands. These ligands are primarily inorganic compounds such as the polyphosphates referred to above. However, U.S. Pat. No. 3,735,001 describes a Tc-99m complex with the organic phosphorus-containing ligand ethane-1-hydroxy-1,1-diphosphonate.

In contrast to the single-organ specific complexes of the prior art, the present invention provides a multi-organ diagnostic system utilizing monophosphonic acids as complexing agents for Tc-99m. By slight chemical variation of the complexing agent, the complexes of the invention can be directed to the kidney, liver or skeleton. These complexes exhibit superior organ specificity over many known imaging agents. They are stable chemically and biologically, of low toxicity, and are safely eliminated from the body. In addition, the complexes of the present invention are water soluble and easily prepared. Their preparation does not require strict adherence to stoichiometric relationships among components or rigorous control of pH, which are problems commonly encountered in the preparation of known Tc-99m complexes.

BRIEF SUMMARY OF THE INVENTION

Briefly, this invention involves reducing an appropriate amount of radioactive pertechnetate ion (99mTcO$_4$) until a major amount of the pertechnetate ion has been reduced to a technetium species having an oxidation state greater than 0 but less than +7, and simultaneously reacting this reduced technetium species with an excess of one of the subsequently described monophosphonic acid complexing agents. The resulting Tc-99m complex is suitable for injection into the blood stream of a mammal when dissolved or dispersed in a biologically sterile, aqueous medium, substantially isotonic with mammalian body fluids. The reduction process may be accomplished chemically through the use of a reducing agent or electrolytically.

Complexes of the present invention are primarily useful in studying the renal, hepatic and skeletal systems of the body. The particular monophosphonic acid ligand used will determine the organ-fate of the complex. The utility of these complexes as radiopharmaceuticals has been elucidated by means of mammalian animal tests.

DETAILED DESCRIPTION OF THE INVENTION

The complexing agents of the invention are substituted and unsubstituted alkyl monophosphonic acids and certain ester derivatives thereof. The complexing agents may be represented by the following formula:

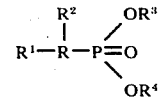

wherein R is an alkyl radical having 1 to 6 carbon atoms; $R^3$ and $R^4$ are either H or an alkyl radical having 1 to 3 carbon atoms; $R^1$ is H or $NH_2$, except when $R^1$ is $NH_2$, then $R^3$ and $R^4$ are H; $R^2$ is H, $NH_2$, or halogen, except when $R^2$ is $NH_2$, then $R^3$ and $R^4$ are H, and when $R^2$ is halogen then $R^1$ is H.

These complexing agents are either commercially available materials or are readily prepared from commercially available materials by conventional methods known in the art.

The selection of a particular complexing agent of the above formula is dependent upon the organ system to be studied and the type of diagnostic information sought.

Kidney Function Agents

High excretion rates are obtained with Tc-99m complexes which are formed from alkyl monophosphonic acids which incorporate one amino group. Best results are obtained when the R substituent of the alkyl phosphonic acid contains 2 to 5 carbon atoms, and the preferred complexing agent of this group is 1-aminobutylphosphonic acid. Because Tc-99m complexes with these ligands are rapidly excreted via the kidney, they may be useful in determining glomerular filtration rates as well as other kidney functions.

Kidney Imaging Agents

The introduction of two amino groups into the longer chain phosphonic acids renders the resulting Tc-99m complexes kidney-specific. Complexes of this group reach their maximum concentration in the mouse kidney approximately one hour after injection and remain relatively highly concentrated in the kidney for several hours. This allows ample time for kidney images to be obtained. Negligible amounts of these complexes are present in other organ systems such as the liver. The preferred complexing agents of this group are compounds wherein the R substituent contains 4 to 6 carbon atoms, especially 1,4-diaminobutyl- and 1,5-diaminopentylphosphonic acids.

Liver Function Agents

Esterification of the phosphonic acids with alkyl alcohols renders the resulting Tc-99m complexes liver-specific. Preferred results are obtained by the esterification of chloromethylphosphonic acid with ethanol to produce chloromethylphosphonic acid diethylester. This complex with Tc-99m is rapidly taken up by the animal liver and concentrations remain high for approximately two hours. As liver concentration decreases, gut uptake increases, indicating that the complex is being metabolized by the liver tissue and safely eliminated from the body. In addition to their usefulness as liver functioning agents, complexes of this group may be used to determine the patency of the bile duct and for gall bladder imaging.

Bone Agents

Unsubstituted alkylphosphonic acid complexes with Tc-99m exhibit bone specificity. Chlorine-substituted phosphonic acids may also be used to form bone-imaging complexes. Complexing agents of this group wherein the R substituent contains one to three carbon atoms are preferred, and the most preferred complexes are Tc-99m-methylphosphonic acid and Tc-99m-chloromethylphosphonic acid. Measurements of radioactivity in the bone compared to the surrounding tissue, obtained with complexes of this group, indicate sharp images of bone tissue are obtained.

Radiopharmaceutical agents from the above-described groups are prepared according to the following method:

1. A solution comprising at least 0.01 but less than 500 millicuries per milliliter of 99m-pertechnetate is reduced to a 99m-technetium species having an oxidation state greater than zero but less than +7.

2. The technetium species of step one is reacted with an excess amount of a complexing agent of the formula:

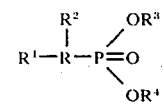

wherein R, $R^1$, $R^2$, $R^3$ and $R^4$ are as defined above.

It is not necessary for reduction of the pertechnetate ion to occur before the complexing agent is added to the solution. It is preferred that the complexing agent be present in the solution before reduction of the pertechnetate ion occurs. Greater yields of complex are obtained when reduction and complex formation are substantially simultaneous. For best results, the reaction mixture is allowed to remain at room temperature for up to 60 minutes, but generally less than 15 minutes is sufficient to insure complete complex formation.

The pertechnetate ion used in the preparation of complexes of the present invention is obtained from a Mo-99 generator in the conventional manner. Eluting or "milking" the generator with an aqueous medium will provide the Tc-99m pertechnetate solution in the form of $M^{+x}$ ($99mTcO_4^-$) where $M^{+x}$ is a pharmaceutically acceptable cation such as a proton, an alkali metal ion, an ammonium ion, or the like, and X is a positive integer less than four. Typically, the elution medium is a saline solution, which provides sodium 99m-pertechnetate ($Na99mTcO_4$).

The technetium in the pertechnetate ion exists in a valence state of +7. In order to form the complexes of the present invention, it is necessary to reduce the technetium to a Tc-99m species having a valence state less than +7 and greater than zero. This reduction can be accomplished chemically with a reducing agent such as Fe (II), asorbic acid, Sn (II), or other suitable reducing agents. Reduction can also be carried out electrolytically.

It is presently preferred to se Sn (II) in the form of $SnCl_2$ as the reducing agent in the preparation of the complexes of the present invention. Normally a large excess of reducing agent is used to insure complete or nearly complete reduction of the pertechnetate ion. From 0.001 to 40 mg. of $SnCl_2$ for each millicurie if pertechnetate is generally used. Sn (II) is very susceptible or oxidation to Sn (IV), and in the higher valence state loses its ability to reduce pertechnetate. For this reason the reaction vial is normally purged with nitrogen or other inert gas to reduce oxidation.

During formation of the complexes it is desirable that the pH of the solution be maintained in the range of about 1 to 3 in order to limit the precipitation of hydrolyzed Sn (II) salts. Regulation of the pH by the addition of extra acid is required in the formation of a few of the complexes of the present invention, especially where the phosphonic acid complexing agent contains one or more amino groups. In forming the liver-specific ester complexes, it is usually necessary to raise the pH of the solution above 7 to prevent precipitation of the complexing agent. As a result, much of the Sn (II) becomes inactivated by precipitation. However, due to the large amount of Sn (II) present, reduction of the pertechnetate presents no problem and the complexes are formed without difficulty. Once the complexes are formed, the pH of the solution may be adjusted, and any Sn (II) precipitate is removed by filtration.

As an alternative to the chemical reduction of 99m-pertechnetate, which necessarily results in the complex solution containing excessive reducing agent and its oxidation product, so-called "clean" complex solutions can be prepared by electrolytic reduction of the pertechnetate.

Electrolytic reduction, like chemical reduction, is best accomplished in the presence of the complexing agent. The solution to be reduced, e.g. Na99mTcO$_4$ and complexing agent, is placed in the cathode chamber of the electrolytic cell, while only the solution containing the complexing agent is placed in the anode chamber. The two chambers are separated by a diaphragm which is permeable to ionic transport, such as a fritted glass disc. The cathode electrode is preferably mercury, either as a mercury pool, a film or an amalgam on a conductive substrate. If a mercury pool is used, it should be constantly stirred in order to maintain sufficient flow of current. The anode may be any commonly used anode material such as carbon, platinum or the like, although platinum is preferred because it has a longer useful life. A calomel electrode is placed in the electrolyte solution of the cathode chamber to measure the potential applied to the cathode. The electrolytic cell is purged with nitrogen.

The electrolytic cell is attached to a battery and a constant voltage between minus 0.6V and minus 1.1V as measured with respect to the reference electrode is applied. The preferred voltage for maximum results is about $-0.85$V. The amperage of the cell is determined by the concentration of pertechnetate in solution, and is normally in the range of 0.1–0.5 mA. Electrolytic reduction of the pertechnetate and simultaneous complex formation is normally complete in 15 to 30 minutes.

Although it may be desirable to provide a radiopharmaceutical preparation that is free from contamination by excessive amounts of a reducing agent such as Sn (II), it has been found that the presence of residual tin in the complex solutions of the present invention does not adversely affect the organ specificity of complexes. This was demonstrated by comparing the organ distribution within the animal body of Tc-99m-methylphosphonic acid prepared by Sn (II) reduction with the same complex prepared by electrolytic reduction. No significant physiological differences were observed between the two complexes.

The amount of Tc-99m needed to produce an amount of radiopharmaceutical suitable for most diagnostic or research purposes is extremely small and is generally in the range of about 0.01 millicuries per milliliter (mCi/ml) of 99m-pertechnetate solution up to about 500 mCi per ml. of such solution. Only about $0.02 \times 10^{-10}$ g. of 99m-pertechnetate dissolved in a milliliter of aqueous medium (e.g., isotonic saline) is needed to provide 0.01 mCi/ml, and less than $100 \times 10^{-10}$ g. of 99m-pertechnetate per milliliter of solution provide enough radioactivity for most uses. The amount of radioactivity per milliliter of 99m-pertechnetate solution obtained from a Mo-99 generator decreases with the age of the generator but it is normally between 0.1 and 60 millicuries.

It is preferred to provide enough complexing agent (ordinarily between $5 \times 10^{-9}$ and $5 \times 10^{-4}$ moles per milliliter of reaction mixture) in order to have an excess over stoichiometry with respect to the Tc-99m in the reaction mixture. In preparing the bone imaging agents of the invention it is particularly desirable to provide a large excess of complexing agent. It has been found that the ratio of the radioactivity of the bone compared to the radioactivity of the surrounding tissue obtained with the complexes can be significantly increased by raising the concentration of complexing agent in the solution. For example, in mice, the "bone to tissue" ratio of Tc-99m-methylphosphonic acid after two hours was more than tripled when the concentration of the complexing agent in solution was increased from 1 mg/ml to 10 mg/ml. Essentially, the same amount of radioactivity was present in each case, but the "bone to tissue" ratio showed marked improvement with a higher concentration of complexing agent.

The amount of complexing agent used is necessarily limited by the toxicity of the compound. The amount of complexing agent injected into a test animal or human patient should preferably be less than 25% of the LD 50 dose in mg. per kg. of body weight, though higher amounts are permissible in veterinary use. Typical LD 50 doses for the preferred complexing agents of this invention range from about 50 mg. to 2 g. per kg. of body weight.

The exact mechanism by which the complexing agents used in this invention become chemically linked to technetium has not be determined. The existence of the complex as distinguished from its precursers can be easily demonstrated, however, by thin layer chromatography. When a solution containing the complex is applied to an unactivated 100 micron - thick silica gel chromatogram sheet having a polyvinyl alcohol binder and a neutral pH (Eastman Chromatogram Sheet 6060 from Eastman Kodak Co.) and acetone is used as the solvent, the complexes remain at the origin while free pertechnetate moves with the solvent front. This method provides a convenient means for testing the solution before use to determine if adequate complex formation has occurred.

When injected into the blood stream of an animal or human subject, the complexes of the invention are dissolved in an aqueous medium, which is biologically sterile and substantially isotonic with mammalian body fluids. The term "substantially isotonic with mammalian body fluids" denotes the situation obtained when the osmotic pressure exerted by the solution in question is sufficiently similar, as compared to a body fluid such as blood, that no dangerous hypo- or hypertonic condition results in the subject when 0.1 ml. (in the case of a mouse) or up to 10 ml. (in the case of a human) of the solution is injected into the blood stream. The preferred aqueous medium for complexes of the invention is a sterile isotonic saline solution. Before injection it may be desirable to filter the solution to eliminate any precipitate which may have formed as well as any bacterial contaminants.

Due to the short half-life of Tc-99m, it is preferred to prepare small batches of complex solutions for immediate use. Batches as small as 0.1 ml. can be adequate for animal studies (e.g., for injection in mice) and batches as large as 50 ml. are convenient for one or more injections into human patients.

A particularly suitable means for preparing the complexes of the invention is to provide the reducing agent and the complexing agent in a preformulated radiopharmaceutical kit for use with a Mo-99 generator. For example, 0.1 (preferably at least 0.5) to 10 ml. of a solution containing 0.5 micromole to about 10 millimoles per ml. of complexing agent and a suitable amount (e.g., 0.01 – 100 micromole per ml.) of reducing agent can be hermetically and aseptically sealed in the same or separate vials having a volume of about 1 to 25 milliliters. The contents of the vial or vials can be further treated (for example, by freeze drying) to produce a dry powder. A preservative such as benzyl alcohol is optionally included in the contents of the vial. The solution in the vial or a solution of the dry powder is preferably substantially isotonic with mammalian body fluids, e.g., human blood. The contents of the vial can be combined with the 99m-pertechnetate-containing, substantially isotonic eluate obtained from the Mo-99 generator. After allowing sufficient time, generally less than 15 minutes, for complex formation to occur, the resulting radiopharmaceutical can be injected into the blood stream of the subject.

Conveniently, the vial-shaped container is provided with a plunger means and a means for attaching a hypodermic needle so that the vial functions as a hypodermic syringe, whereby, after preparation of the solution the contents can be injected parenterally without being transferred to another container or syringe.

Radioactivity measurements are made in the conventional manner for a period beginning after injection and lasting up to about 24 hours, depending upon the organ to be studied and the nature of the diagnosis. The preferred times for mesurement using complexes of the present invention are within 1 hour for kidney function tests, 0.5–4 hours for kidney imaging; 0.5–6 hours for liver function, and 0.5–6 hours for bone imaging.

The invention is further illustrated by the following non-limiting examples:

EXAMPLE 1

Tc-99m-methylphosphonic acid (1 mg. of methylphosphonic acid per ml. of solution)

Ten mg. of methylphosphonic acid were dissolved in 5 ml. of isotonic saline solution (0.9% NaCl) in a clean glass vial having a volume of 20 ml. To the vial were added 400 microcuries of $99mTcO_4$ in a 2 ml. of isotonic saline solution. The vial was evacuated (~5 mmHg) and purged with nitrogen. A solution of 0.4 mg. of Sn (II) as $SnCl_2.2H_2O$ in 0.1 ml. ethanol was then added. After the vial was set aside for 50 minutes, 3 ml. of isotonic saline solution were added to dilute its contents to 10 ml.

The solution containing the Tc-99m-methylphosphonic acid complex (pH 2.4) was sterilized by filtration through a 0.2 μm filter, and 0.1 ml. of the solution was injected into the tail veins of white Swiss Webster mice. The mice were sacrificed at appropriate time periods, dissected and individual organs were assayed for Tc-99m activity using a Packard 410A gamma spectrometer with a NaI well crystal detector. Distribution of the complex within the animal is shown in the following table.

TABLE I

Distribution of
Tc-99m-methylphosphonic acid [Tc-99m-$CH_3PO(OH)_2$]

| Organ | Hours After Injection (Percent of Total Injected Radioactivity) | | | | | |
|---|---|---|---|---|---|---|
| | 0 | 1/2 | 1 | 2 | 4 | 24 |
| Lungs | 5.6% | 0.4 | 0.5 | 0.4 | 0.2 | 0.2 |
| Liver | 22.5 | 1.3 | 2.1 | 1.9 | .15 | 1.0 |
| Spleen | 0.3 | 0.1 | 0.1 | 0.08 | 0.04 | 0.1 |
| Kidney | 12.0 | 2.1 | 2.5 | 2.2 | 2.0 | 1.0 |
| Stomach | 1.7 | 0.3 | 0.3 | 0.8 | 0.3 | 0.2 |
| Gut | 14.4 | 2.2 | 2.9 | 3.2 | 2.2 | 1.1 |
| Pancreas | 1.1 | 0.1 | 0.09 | 0.14 | 0.02 | 0.1 |
| Carcass | 42.5 | 24.1 | 21.2 | 34.0 | 19.8 | 25.5 |
| Urine and Feces | 0.0 | 69.4 | 70.4 | 57.3 | 73.8 | 70.8 |

These data indicate that the complex becomes rapidly localized in the skeleton (carcass). Bone to tissue ratio after 2 hours was 2.1.

EXAMPLE 2

Tc-99m-methylphosphonic acid (10 mg. of methylphosphonic acid per ml. of solution)

One hundred mg. of methylphosphonic acid were dissolved in 5 ml. of isotonic saline solution (0.9% NaCl) in a clean glass vial having a volume of 20 ml. To the vial were added 130 microcuries of $99mTcO_4$ in 4 ml. of isotonic saline solution. The vial was evacuated (~5 mmHg) and purged with nitrogen. One ml. of a 5% $SnCl_2$ solution in 0.1N HCl [7.9 mg. of Sn (II)] was added. After the vial was set aside for 15 minutes, the pH of the solution was raised to 5.8 by the addition of 1N NaOH.

The solution containing the Tc-99m-methylphosphonic acid complex was sterilized by filtration through a 0.2 μm filter. The complex was evaluated in mice using the method described in Example 1. Distribution of the complex within the animal is shown in the following table.

TABLE II

Distribution of
Tc-99m-methylphosphonic acid [Tc-99m-$CH_3PO(OH)_2$]

| Organ | Hours After Injection (Percent of Total Injected Radioactivity) | |
|---|---|---|
| | 0 | 2 |
| Heart | 4.4 | 0.1 |
| Lung | | |
| Liver | 21.63 | 0.6 |
| Kidney | 9.48 | 0.69 |
| Stomach | 1.14 | 0.15 |
| Gut | 12.91 | 0.95 |
| Spleen | 1.30 | 0.03 |
| Pancreas | | |
| Carcass | 49.11 | 26.07 |
| Urine and Feces | 0.0 | 71.4 |

The bone to tissue ratio of this complex after two hours was 7.6

EXAMPLE 3

Tc-99m-aminobutylphosphonic acid

Twenty-five mg. of 1-aminobutylphosphonic acid were dissolved in 3 ml. of isotonic saline solution (0.9% NaCl) in a clean glass vial having a volume of 5 ml. To the vial were added 55 microcuries of 99mTcO$_4$ in 0.1 ml. of isotonic saline solution. The vial was evacuated (~5 mmHg) and purged with nitrogen. A solution of 0.04 mg. of Sn (II) as SnCl$_2$.2H$_2$O in 0.1 ml. ethanol was then added. After the vial was set aside for 30 minutes, 5 ml. of isotonic saline solution was added to dilute the contents to 5 ml. The solution (pH4) was sterilized by filtration through a 0.2 $\mu$m filter.

The Tc-99m-1-aminobutylphosphonic acid complex was evaluated in mice according to the method described in Example 1. Distribution of the complex within the animal is shown in the following table.

TABLE III

Distribution of
Acid
[Tc-99m-CH$_3$CH$_2$CH$_2$CHNH$_2$PO(OH)$_2$]

| | Hours After Injection (Percent of Total Injected Radioactivity) | | | | |
|---|---|---|---|---|---|
| Organ | 0 | 1/2 | 1 | 2 | 4 |
| Lungs | 4.6 | 0.9 | 0.4 | 0.2 | 0.2 |
| Liver | 18.5 | 2.5 | 1.4 | 1.0 | 0.7 |
| Spleen | 0.2 | 0.1 | 0.1 | 0.1 | 0.02 |
| Kidney | 17.5 | 1.9 | 0.9 | 0.8 | 0.9 |
| Stomach | 1.1 | 0.3 | 0.2 | 0.4 | 0.2 |
| Gut | 11.5 | 2.4 | 1.1 | 1.0 | 4.8 |
| Thyroid | 1.7 | 0.2 | 0.1 | 0.1 | 0.04 |
| Pancreas | 0.8 | 0.1 | 0.02 | 0.03 | 0.02 |
| Carcass | 44.1 | 17.5 | 10.8 | 5.9 | 6.2 |
| Urine and Feces | 0.0 | 74.2 | 85.0 | 90.7 | 86.6 |

These data indicate the complex is rapidly excreted via the kidney.

EXAMPLE 4

Tc-99-m-1,5-diaminopentylphosphonic acid

Twenty-five mg. of 1,5-diaminopentylphosphonic acid dissolved in 3 ml. of isotonic saline solution (0.9% NaCl) in a clean glass vial having a volume of 5 ml. The pH of the solution was lowered to 2 by the addition of 0.1 ml. of 1N HCl. To the contents of the vial were added 43 microcuries of 99m-TcO$_4$ in 0.1 ml. of isotonic saline solution. The vial was evacuated and purged with nitrogen. A solution of 0.04 mg. of Sn (II) as SnCl$_2$.2H$_2$O in 0.1 ml. ethanol was then added. After the vial was set aside for 45 minutes, th pH of the solution was raised to 5 by the addition of 0.1 ml. of 1N NaOH. The solution was sterilized by filtration through a 0.1 $\mu$m filter.

The Tc-99m-diaminopentylphosphonic acid complex was evaluated in mice using the method of Example 1. Distribution of the complex within the animal is shown in the following table.

TABLE IV

Distribution of
Tc-99m-1,5-diaminopentylphosphonic acid
[Tc-99m-CH$_2$NH$_2$(CH$_2$)$_3$CHNH$_2$PO(OH)$_2$]

| | Hours After Injection (Percent of Total Injected Radioactivity) | | | | |
|---|---|---|---|---|---|
| Organ | 0 | 1/2 | 1 | 2 | 24 |
| Lungs | 10.2% | 0.9 | 0.4 | 0.3 | 0.0 |
| Liver | 15.5 | 2.1 | 1.7 | 0.7 | 0.3 |
| Spleen | 0.2 | 0.1 | 0.03 | 0.02 | 0.0 |
| Kidneys | 12.1 | 26.5 | 27.8 | 26.8 | 7.2 |
| Stomach | 1.7 | 0.6 | 0.2 | 0.1 | 0.2 |
| Gut | 10.5 | 2.0 | 1.7 | 0.7 | 0.1 |
| Pancreas | 1.0 | 0.1 | 0.04 | 0.04 | 0.0 |
| Carcass | 49.0 | 20.4 | 13.6 | 10.0 | 9.1 |
| Urine and Feces | 0.0 | 47.3 | 55.0 | 61.3 | 83.2 |

These data indicate high uptake of the complex by the kidney without rapid excretion.

EXAMPLE 5

Tc-99m-chloromethylphosphonic acid diethylester

Twenty-five microliters of chloromethylphosphonic acid diethylester were dissolved in 3 ml. of isotonic saline solution (0.9% NaCl) in a clean glass vial having a volume of 10 ml. The pH of the solution was raised to 7 by the addition of 25 ml. of 1N NaOH. To the vial were added 90 microcuries of 99m-TcO$_4$ in 1 ml. of isotonic saline solution. The vial was evacuated and purged with nitrogen. A solution of 0.04 mg. of Sn (II) as SnCl$_2$.2H$_2$O in 0.1 ml. ethanol was then added. After the vial was set aside for 20 minutes, the solution was sterilized by filtration through a 0.2 $\mu$m filter.

The Tc-99m-chloromethylphosphonic acid diethylester complex was evaluated in mice using the method of Example 1. Results are shown in the following table.

TABLE V

Distribution of
Tc-99m-chloromethylphosphonic acid diethylester
[Tc-99m-ClCH$_2$PO(OC$_2$H$_5$)$_2$]

| | Hours After Injection (Percent of Total Injection Radioactivity) | | | | |
|---|---|---|---|---|---|
| Organ | 0 | 1/2 | 1 | 2 | 4 |
| Lungs | 8.3 | 1.8 | 3.4 | 1.3 | 1.0 |
| Liver | 29.7 | 52.8 | 37.2 | 26.2 | 19.2 |
| Spleen | 0.3 | 0.9 | 0.4 | 0.7 | 0.4 |
| Kidney | 7.0 | 3.7 | 6.0 | 4.7 | 2.3 |
| Stomach | 1.0 | 0.6 | 0.6 | 0.5 | 0.4 |
| Gut | 12.0 | 29.5 | 35.5 | 48.2 | 15.7 |
| Pancreas | 0.8 | 0.3 | 0.2 | 0.2 | 0.1 |
| Carcass | 40.9 | 18.4 | 12.5 | 12.8 | 7.3 |
| Urine and Feces | 0.0 | 8.1 | 4.1 | 5.4 | 53.6 |

Data indicates the complex is preferentially eliminated via the liver.

EXAMPLE 6

Electrolytic Reduction (Tc-99m-methylphosphonic acid)

The electrolysis was performed in a glass cell which contained a fritted glass disc to separate the cathode from the anode. The cathode consisted of a mercury pool (~5 cm in diameter) which was stirred at the surface by a magnetic stirring bar to provide a constantly renewed mercury/electrolyte interface. A platinum sheet (2 × 5 cm) was used as the anode and a saturared calomel electrode was used as the reference electrode.

About 250 mg. of methylphosphonic acid was dissolved in 5 ml. of isotonic saline solution (0.9% NaCl) and placed in both the anode chamber and the cathode chamber of the electrolysis cell. To the cathode chamber were added 120 microcuries of 99m-TcO₄ in isotonic saline solution (pH 2.1).

The electrolysis was conducted under nitrogen at −0.85 V versus S.C.E. and at an initial current of 0.2 mA. After 15 minutes of electrolysis, the pH of the electrolyte was raised to 5. The solution was then filtered through a 0.22 μm filter and diluted to 10 ml. with isotonic saline solution.

The Tc-99m-methylphosphonic acid complex was evaluated in mice using the method of Example 1. Results were as follows:

TABLE VI

Distribution of
Tc-99m-methylphosphonic acid
Prepared by Electrolytic Reduction of 99m-TcO₄

Hours After Injection
(Percent of Total Injected Tc-99m as a Function of Time)

| Organ | 0 | 2 |
|---|---|---|
| Lung and Heart | 8.6 | 0.3 |
| Liver | 18.1 | 2.1 |
| Kidneys | 6.7 | 0.7 |
| Stomach | 1.1 | 2.8 |
| Gut | 9.9 | 3.5 |
| Spleen and Pancreas | 1.1 | 0.2 |
| Carcass | 54.5 | 28.6 |
| Urine and Feces | 0.0 | 61.8 |

These data indicate substantially the same biological distribution is obtained with complexes prepared by electrolytic reduction as compared with those obtained with chemical reduction of 99m-TcO₄.

What is claimed is:

1. A process for preparing a radiopharmaceutical comprising reducing a solution comprising at least 0.01 but not more than 500 millicuries per milliliter of 99m-pertechnetate ion until at least 50 mole percent of said 99m-pertechnetate ion has been reduced to a 99m-technetium species having an oxidation state greater than zero, but less than +7, and reacting said 99m-technetium species with a molar excess of a phosphonic acid complexing agent of the formula.

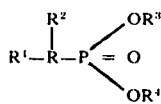

wherein R is an alkylene radical having 1 to 6 carbon atoms; $R^3$ and $R^4$ are either H or an alkyl radical having 1 to 3 carbon atons; $R^1$ is H or $NH_2$, except when $R^1$ is $NH_2$, then $R^3$ and $R^4$ are H; and $R^2$ is H, $NH_2$ or halogen, except when $R^2$ is $NH_2$, then $R^3$ and $R^4$ are H, and when $R^2$ is halogen, then $R^1$ is H.

2. A process according to claim 1 wherein 0.001 to 40 mg. of a Sn (II) compound is added for each millicurie of 99m-pertechnetate ion to bring about reduction of said 99m-pertechnetate ion.

3. A process according to claim 2 wherein SnCl₂ is the reducing agent.

4. A process according to claim 1 wherein said 99m-pertechnetate ion is reduced electrolytically.

5. A process according to claim 1 wherein the complexing agent is a phosphonic acid of the formula:

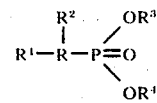

wherein R is an alkyl radical having 2 to 5 carbon atoms; $R^3$ and $R^4$ are H; $R^1$ is $NH_2$; $R^2$ is H; and the resulting radiopharmaceutical is useful for studying kidney functioning.

6. A process according to claim 5 wherein the complexing agent is 1-aminobutylphosphonic acid.

7. A process according to claim 1 wherein the complexing agent is a phosphonic acid of the formula:

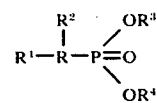

wherein R is an alkyl radical having 4 to 6 carbon atoms; $R^3$ and $R^4$ are H; $R^1$ is $NH_2$; $R^2$ is $NH_2$; and the resulting radiopharmaceutical is useful as a kidney imaging agent.

8. A process according to claim 7 wherein the complexing agent is 1,4-diaminobutylphosphonic acid.

9. A process according to claim 7 wherein the complexing agent is 1,5-diaminopentylphosphonic acid.

10. A process according to claim 1 wherein the complexing agent is a phosphonic acid compound of the formula:

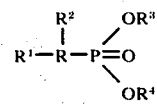

wherein R is an alkyl radical having 1 to 3 carbon atoms; $R^3$ and $R^4$ are H; $R^1$ is H or halogen; $R^2$ is H; and the resulting radiopharmaceutical is a bone imaging agent.

11. A process according to claim 10 wherein the complexing agent is methylphosphonic acid.

12. A process according to claim 10 wherein the complexing agent is chloromethylphosphonic acid.

13. A process according to claim 1 wherein the complexing agent is chloromethylphosphonic acid diethylester, and the resulting radiopharmaceutical is useful in studying liver functioning.

14. A process according to claim 1 wherein the radiopharmaceutical is dissolved in a biologically sterile, substantially isotonic aqueous medium.

15. A process according to claim 14 wherein the radiopharmaceutical is dissolved in a sterile saline solution.

16. A device for the preparation of a radiopharmaceutical solution containing a complex of Tc-99m which comprises a vial-shaped container having a volume of from 5 to 25 ml. in which are aseptically and hermetically sealed from about 0.5 micromoles to 10 millimoles of a phosphonic acid complexing agent of the formula:

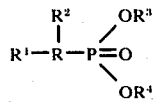

wherein R is an alkyl radical having 1 to 6 carbon atoms; $R^3$ and $R^4$ are either H or an alkyl radical having 1 to 3 carbon atoms; $R^1$ is H or $NH_2$, except when $R^1$ is $NH_2$, then $R^3$ and $R^4$ are H; and $R^2$ is H, $NH_2$, or halogen, except when $R^2$ is $NH_2$, then $R^3$ and $R^4$ are H, and when $R^2$ is halogen then $R^1$ is H; and from 0.01 to 100 micromoles of a pharmaceutically acceptable reducing agent for 99m-pertechnetate.

17. A device according to claim 16 wherein the complexing agent is selected from the group consisting of:
 1-aminobutylphosphonic acid
 1,4-diaminobutylphosphonic acid
 1,5-diaminopentylphosphonic acid
 methylphosphonic acid
 chloromethylphosphonic acid diethylester.

18. A device according to claim 16 wherein the reducing agent is $SnCl_2$.

19. A device according to claim 16 wherein the vial has a means for hypodermic injection of the contents.

20. The radiopharmaceutical prepared by reducing a solution comprising at least 0.01 but less than 500 millicuries per milliliter of 99m-pertechnetate ion until at least 50 mole percent of said 99m-pertechnetate ion has been reduced to a 99m-technetiun species having an oxidation state greater than zero but less than +7, and reacting said 99m-technetium species with a molar excess of a phosphonic acid complexing agent of the formula:

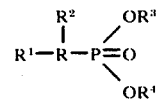

wherein R is an alkylene radical having 1 to 6 carbon atoms; $R^3$ and $R^4$ are either H or an alkyl radical having 1 to 3 carbon atoms; $R^1$ is H or $NH_2$, except when $R^1$ is $NH_2$, then $R^3$ and $R^4$ are H; and $R^2$ is H, $NH_2$ or halogen, except when $R^2$ is $NH_2$, then $R^3$ and $R^4$ are H, and when $R^2$ is halogen, then $R^1$ is H.

* * * * *

UNITED STATES PATENT AND TRADEMARK OFFICE
CERTIFICATE OF CORRECTION

PATENT NO. : 3,976,762
DATED : August 24, 1976
INVENTOR(S) : GUNTER A. KOHLER AND GARY M. PESTEL It is certified that error appears in the above-identified patent and that said Letters Patent are hereby corrected as shown below:

Col. 4, line 43, change "se" to -- use --.

Col. 4, line 48, change "if" to -- of --.

Col. 4, line 50, change "or" to -- to --.

Col. 6, line 27, change "be" to -- been --.

Col 9, Table III, in heading, delete the word "acid" and insert the following: -- Tc-99m-1-aminobutylphosphonic acid --.

Col 9, line 55, change "0.1" to -- 0.2 --.

Signed and Sealed this

Second Day of November 1976

[SEAL]

Attest:

RUTH C. MASON
Attesting Officer

C. MARSHALL DANN
Commissioner of Patents and Trademarks